United States Patent [19]

Taylor

[11] Patent Number: 5,302,169
[45] Date of Patent: Apr. 12, 1994

[54] POST OPERATIVE KNEE BRACE

[75] Inventor: Dean A. Taylor, Vancouver, Canada

[73] Assignee: Generation II Orthotics Inc., Richmond, Canada

[21] Appl. No.: 1,204

[22] Filed: Jan. 4, 1993

[51] Int. Cl.⁵ .............................................. A61F 5/00
[52] U.S. Cl. ........................................ 602/16; 602/26
[58] Field of Search ..................... 602/16, 23, 26, 62; 128/882; 623/27, 39

[56] References Cited

U.S. PATENT DOCUMENTS

| | | | |
|---|---|---|---|
| 3,799,158 | 3/1974 | Gardner | 602/26 X |
| 3,902,482 | 9/1975 | Taylor | 602/26 X |
| 4,241,730 | 12/1980 | Helfet | 602/26 |
| 4,256,097 | 3/1981 | Willis | 602/26 X |
| 4,686,969 | 8/1987 | Scott | 602/26 |
| 4,854,308 | 8/1989 | Drillio | 602/26 X |
| 5,002,045 | 3/1991 | Spademan | 602/26 X |

Primary Examiner—Richard J. Apley
Assistant Examiner—Linda C. M. Dvorak

[57] ABSTRACT

An orthopaedic brace having a pair of arms to be secured to wearer's body. There is a pivotable joint between the arms to allow pivoting of the knee while supporting the knee. According to the invention there is a joint in the brace to allow controlled inclination of each arm relative to the pivotable joint. A method of bracing a knee following high tibial osteotomy is also disclosed. According to the method aspect the brace as described above is located about the knee and the arms are adjusted to allow controlled inclination of each arm relative to the pivotable joint to provide the required bracing of the required inclination.

17 Claims, 4 Drawing Sheets

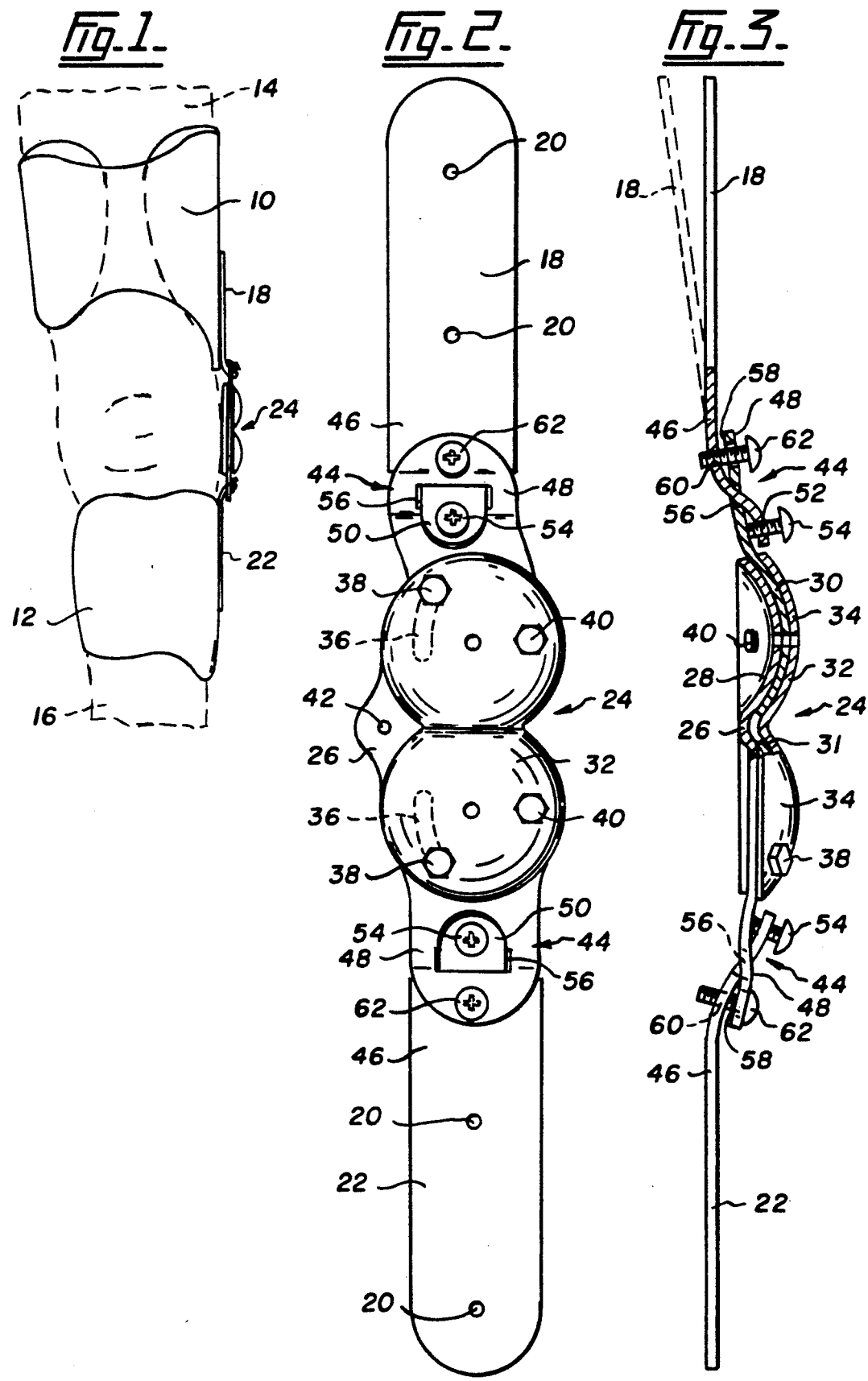

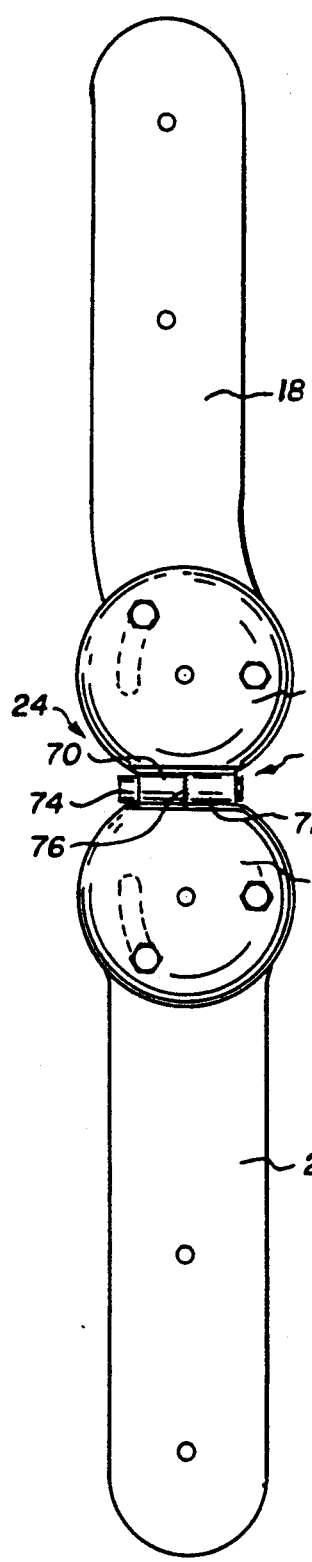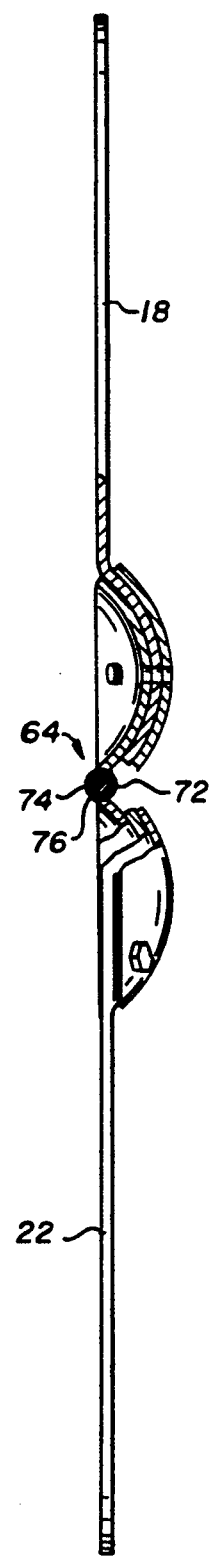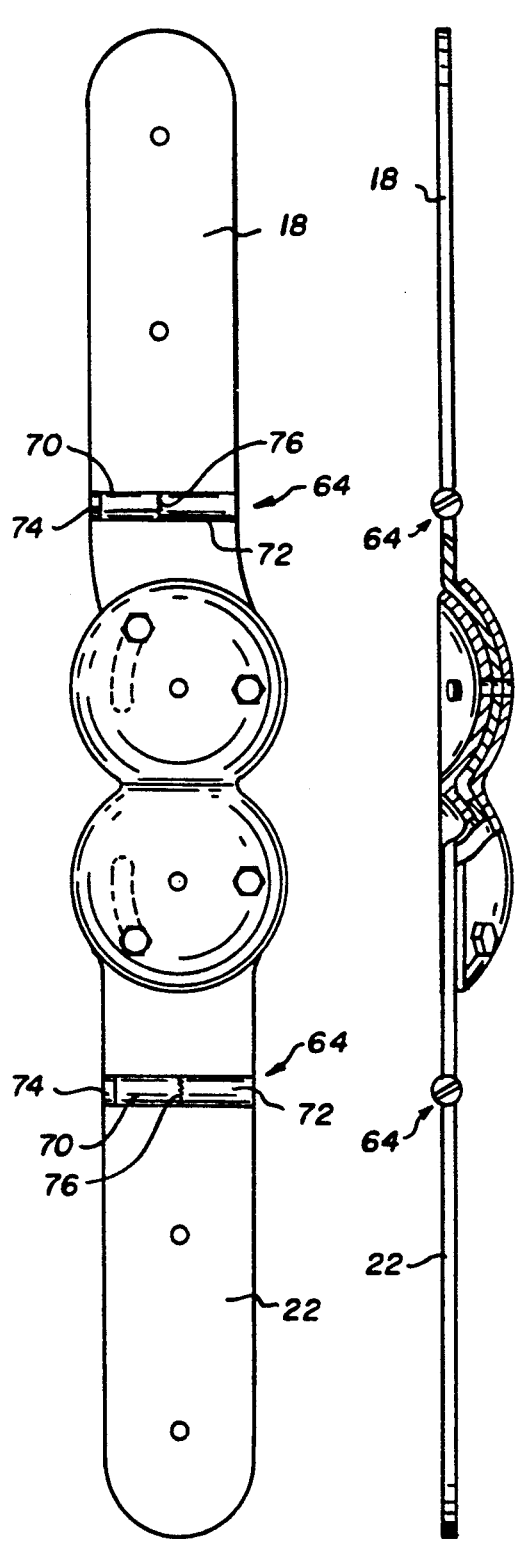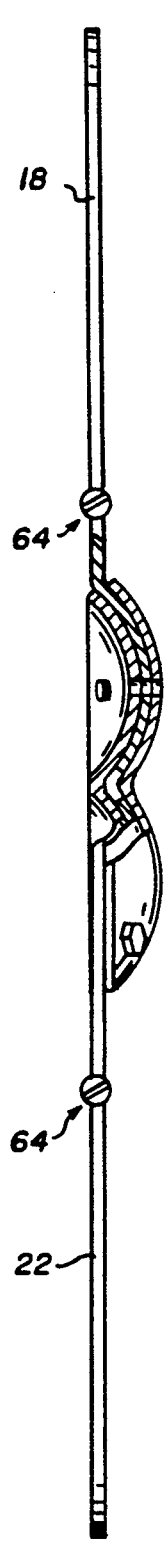

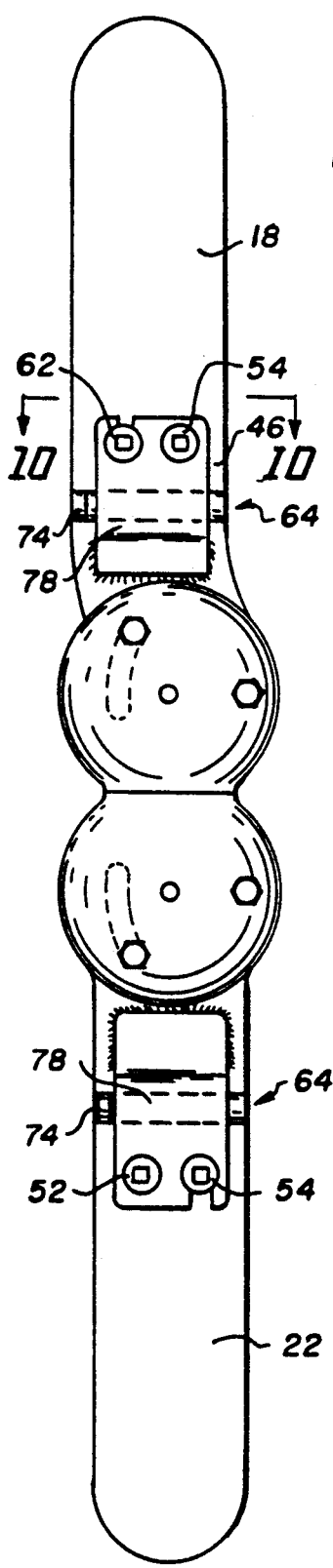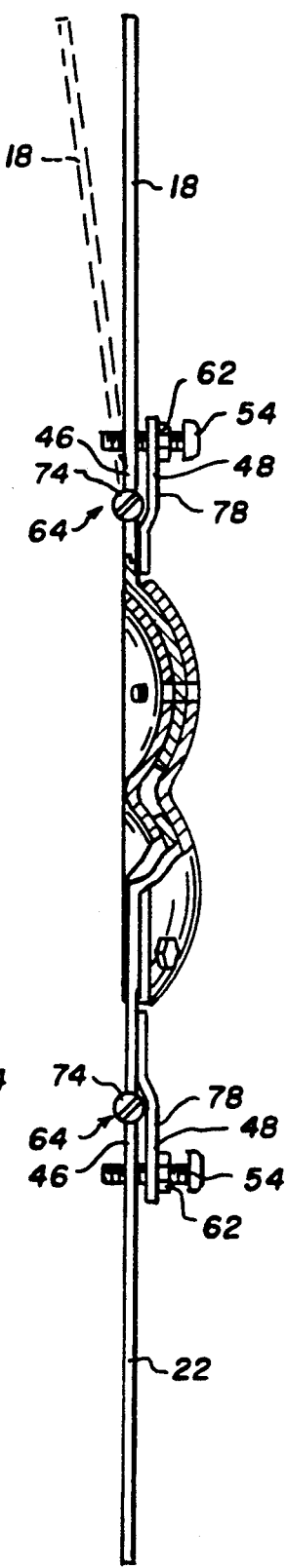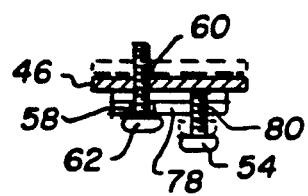

POST OPERATIVE KNEE BRACE

FIELD OF THE INVENTION

This invention relates to an orthopaedic brace and to a method of bracing a knee using that brace.

DESCRIPTION OF THE PRIOR ART

U.S. patent application Ser. No. 934,819 filed Aug. 24, 1992, which is a continuation-in-part of application Ser. No. 697,146 filed May 8, 1991, teaches a method of reducing the effects of unicompartmental osteoarthritis of the knee. The method comprises applying a force to the knee as the knee moves to extension. The force is applied on that side of the knee remote from the compartment having osteoarthritis. The force is applied at about 10° to 15° posterior of the normal axis of rotation of the knee.

This method has attracted considerable interest and has achieved excellent results. It is a non-invasive treatment of uni-compartmental osteoarthritis. This complaint, which may occur in the medial compartment or in the lateral compartment of the knee, is a malfunction of the knee where uneven distribution of pressure occurs across the knee. This produces excessive wear on the inside of the knee joint in medial compartmental osteoarthritis and on the outside of the knee joint in lateral compartmental osteoarthritis. A healthy knee joint has an even distribution of pressure medially and laterally and the space between the femur, or thigh bone, and the tibia, or shin bone, is symmetrical and approximately one quarter inch. If uni-compartmental osteoarthritis is induced, for example by injury or by aging, the space between the femur and the tibia decreases. The problem may progress to the extent that the space is eliminated and the femur contacts the tibia. Erosion of the tibia may then result.

With the disease there is a change in the normal angle between the femur and tibia. For example if the patient stands in 2° of varus, or bow-leggedness, then with the advancement of the disease the angle will increase to, for example, about 5° varus. Debilitation of the knee will continue and the angle is increased further.

Prior to the development of the above method of the above United States patent application, uni-compartmental joint disease was treated in three ways:

1. Anti-inflammatory and analgesic compounds:
2. High tibial osteotomy: and
3. Total knee arthroplasty (TKA) or knee replacement.

High tibial osteotomy involves the removal of a triangular segment of the tibia as a means of correcting the excessive inclination induced by uni-compartmental osteoarthritis. After surgery the knee is encased in a cast that immobilizes the knee.

U.S. Pat. No. 3,902,482 issued Sep. 2, 1975 relates to an orthopaedic brace having portions attachable to parts of a wearer's body on opposite sides of a body joint. There is a mechanical joint comprising a bearing plate on an end of each brace portion near the body joint. A link extends across the body joint and has a bearing plate on each end. The bearing plates of the link overlap the bearing plates of the brace portion to provide dual bearings. A pivot interconnects the bearing plates of each of the dual bearings. The pivot provides each of the dual bearings with a plurality of transverse pivotal axes, which are shiftable to accommodate the natural pivotal movement of the body joint. This arrangement is such that one of the brace portions is movable away from and toward the other of the brace portions as the body joint is flexed and straightened.

Braces of this type have achieved excellent acceptance. They are usually custom made for a patient. They are light and unobtrusive to wear. Although the pivot is light and seemingly simple in construction, it has excellent ability to follow the relatively complex motion of the knee, unlike the braces that preceded it.

Since the above United States patent issued a substantial number of sophisticated orthopaedic braces have come onto the market.

SUMMARY OF THE INVENTION

The present invention seeks to use a brace of the type generally described and claimed in U.S. Pat. No. 3,902,482 modified to be useful as a post-operative brace after a patient has had high tibial osteotomy.

Accordingly, and in a first aspect, the present invention provides an orthopaedic brace comprising a pair of first arms to be secured to a wearer's body, a pivotable joint between said first arms to allow pivoting of the knee while supporting the knee, the improvement comprising, a joint in the brace to allow controlled inclination of each first arm relative to the pivotable joint.

In a further aspect, the invention is a method of bracing the knee of a patient following high tibial osteotomy comprising locating a brace, as discussed above, about the knee, following surgery, and adjusting the inclination of the arms of the brace to provide the required bracing at the required inclination.

DESCRIPTION OF THE DRAWINGS

The invention is illustrated in the drawings in which:

FIG. 1 is a front view showing part of a brace according to the present invention in position on a leg of a patient;

FIG. 2 is a front view of a brace according to this invention;

FIG. 3 is a side elevation of the brace of FIG. 2;

FIG. 4 is a front view of a further embodiment of a brace according to the present invention;

FIG. 5 is a side elevation of the brace of FIG. 4, partially in section;

FIG. 6 is a front view of a part of a brace according to the present invention;

FIG. 7 is a side elevation of the brace of FIG. 6, partially in section;

FIG. 8 is a front view of a further embodiment of the present invention;

FIG. 9 is a side elevation of the brace of FIG. 10; partially in section;

FIG. 10 is a detail of the brace of FIGS. 8 and 9; and

DESCRIPTION OF THE PREFERRED EMBODIMENTS

Figure 11:
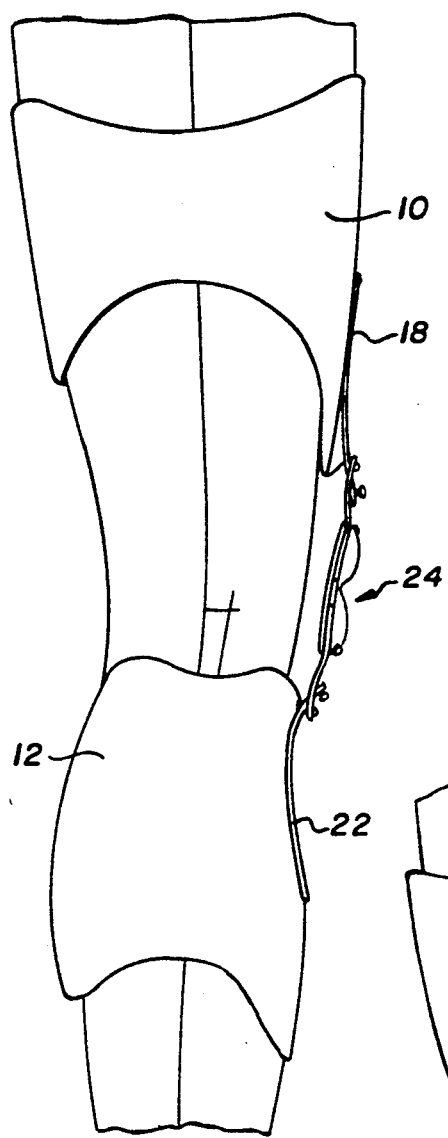
FIGS. 11 to 13 illustrate the method according to the present invention.

First, in the interest of clarity the various straps and supports used to locate the brace on the leg and, in certain circumstances, to apply pressure to the leg are not shown in the drawings. They do not form a feature of the present invention but are wholly within the prior art.

The drawings show a brace having an upper cuff 10 and a lower cuff 12. The upper cuff 10 fits around the thigh 14 of a wearer and the lower cuff 12 around the upper calf 16.

Cuff 10 is attached to a first arm 18 and located by screws extending through the cuff 10 to engage in threaded openings 20 in the arm 18—see FIG. 2. A second arm 22 is attached to cuff 12 in the same manner. The brace of the present invention is secured to a wearer's body by use of the cuffs 10 and 12. There is a pivotable joint 24 between the arms 20 and 22 that allows pivoting of the knee even when the brace is present. Although it does not form a feature of the present invention, the pivotable joint 24 comprises, as shown most clearly in FIG. 3, an inner bearing plate 26 comprising two part spherical projections 28. These part spherical projections 28 each engage within a correspondingly shaped bearing plate 30 and 31 on the end of each arm 18 and 22. These bearing plates 30 and 31 are, in turn, received within an outer bearing plate 32 again comprising, like the inner bearing plate 26, two part spherical members 34 that are a close fit over the bearing plates 30 and 31 on the end of the arms 18 and 22.

Bearing plates 30 and 31 each have slots 36 formed in them engaged by a bolt 38 extending through a clear hole (not shown) in the outer plate 32 to engage a threaded hole (not shown) in the inner plate 26. Pivot points are each defined by a second bolt 40 extending through a clear opening in the outer plate 32, through a clear opening in a bearing plate 30 or 31 to engage a threaded opening in the inner plate 26. The inner plate 26 is shown with an opening 42 that receives a strap, that is not shown and is not part of the present invention.

According to the invention the embodiment of FIGS. 2 and 3 has a joint 44 in each arm 18 and 22. The joint 44 allows controlled inclination of each arm 18 or 22 relative to the pivotable joint 24. In the illustrated embodiment the joint 44 in each arm 18 or 22 is formed close to the pivotable joint 24 of the brace. Each arm 18 or 22 is formed in at least two parts. A first part 46 extends along the leg of the wearer, as shown particularly in FIG. 1 and a second part 48 extends from the bearing plates 30 or 31.

There is a tab 50 on each first part 46. Tab 50 has a threaded opening 52 that receives a screw 54. There is an opening 56 in each second part 48 that receives a tab 50 and there are means to secure the first and second parts 46 and 48 together and to lock them in a predetermined position. Screws 54 provide means to move the first and second parts 46 and 48 relative to each other to set the predetermined position.

As shown in FIG. 3, the means to secure the parts 46 and 48 and to lock the parts in a predetermined position comprises a clear opening 58 in each second part 48, adjacent the opening 56 through which the tab 50 extends. There is a threaded opening 60 in the first part 46 that receives a screw 62.

The brace of FIGS. 2 and 3 is used as follows.

Prior to surgery the patient will be fitted with a brace according to FIGS. 2 and 3, custom made as is usual with this type of brace. That is to say the cuffs 10 and 12, in particular, will be moulded to match the patient's leg. In addition, the arms 18 and 22 will be of the appropriate length for the patient and will ensure that the pivotal joint 24 is in the proper position relative to the patient's knee.

After the operation the surgeon will adjust the brace in precisely the correct manner for that patient to ensure that the correct adjustment is applied to support the knee following surgery. The surgeon can apply varus, that is bow-leggedness, or valgus, that is knock-kneedness, as deemed fit.

The appropriate setting is achieved in the following way.

First, the screws 62 are loosened which means that the first part 46 of each arm can move relative to the second part 48 of the arm. The screws 54 may also be slackened if necessary. Once the screws 62 are loose, the brace is placed on the leg of the patient. The screws 54 are tightened in openings 54 until it makes contact with the part 48 of the arm 18 and 22. When the surgeon is satisfied that the correct position is established in this way, the screws 62 will be tightened to secure that position. FIG. 3 illustrates slackening of the top screw 62 so that it is in a position in which part 46 can be adjusted, as shown by the broken lines in FIG. 3. FIG. 3 also shows, at the bottom, a correctly adjusted brace, that is both the screws 54 and 62 are tightened.

FIGS. 4 and 5 illustrate a further embodiment of the invention in which controlled inclination of each arm relative to the pivotable joint is achieved by a hinge 64 formed in the pivotable joint.

Many details of the embodiment of FIGS. 4 and 5 are the same as in FIGS. 1 to 3 and, accordingly, the same reference numerals are used as appropriate. No further discussion of these features is included.

However, FIGS. 4 and 5 shows a pivotable joint 24 formed in two parts, a first 66 and a second part 68. The hinge 64 is also formed in two parts, with one part 70 attached to the first part 66 of the pivotable joint and the second part 72 attached to the second part 68 of the pivotable joint. The second part 72 is formed with an internal thread. There is a threaded hinge pin 74, extending through the first and second parts 70 and 72 and engaging the thread in the second part 72. The arrangement is such that slackening and tightening of the pin 74 in the threaded part 72 allows setting then locking of the brace in a predetermined position with the arms 18 and 22 at a controlled inclination to the pivotable joint 24. Parts 70 and 72 of the hinge have abutting internal surface at 76 and, instead of relying on contact of flat internal surfaces, FIGS. 4 shows the formation of mutually engagable serrations at 76 to assist locking at the predetermined position.

To use the brace of FIGS. 4 and 5, the same general procedure is followed as discussed for the embodiment of FIGS. 2 and 3 but adjustment of the relative positions of the arms 18 and 22 is achieved by loosening the hinge pin 74, moving the internal surfaces of the hinge parts 70 and 72 away from each other and inclining the arms 18 and 22 using the serrations at 76 which, typically, are precisely machined. When the appropriate setting is fixed the hinge pin 74 is tightened in position in the second part 72 to fix the setting.

The embodiment of FIGS. 6 and 7 may be considered a combination of the embodiment of FIGS. 2 and 3 and the embodiment of FIGS. 4 and 5 in that there is a joint in each arm, as in FIGS. 2 and 3, but that joint is a hinge, as in FIG. 3, 4 and 5. Again, as appropriate, the same reference numerals are used, the hinges being described as for FIG. 4. Use of this embodiment is as for FIGS. 4 and 5 except that each hinge 64 is set by the surgeon as appropriate.

The embodiment of FIGS. 8 to 10 may be considered a combination of all the preceding embodiments. There are hinged joints 64 in each arm 18 and 22 but adjustment of the joints 64 is not achieved by threading of the hinge pins 74 but by the use of screws, as in the embodiment of FIGS. 2 and 3. Hinge pins 74 need not be threaded although it is a convenient way of ensuring that they remain in position in the brace. In the brace of FIGS. 8 to 10 there is a tab 78 extending from the second part 48, over the first part 46 of each leg. As in FIGS. 2 and 3 there is a threaded opening 60 in each first part 46 that receives a screw 62 extending through a clear opening 58 in the tab 78. There is a threaded opening 80 in the tab 78 and the screw 54 extends through that threaded opening 80 to abut the first part 46. Control of the inclination using these screws is as for the embodiment of FIGS. 2 and 3.

The following experimental procedure illustrates the use of a brace according to FIGS. 2 and 3.

The patient was a female, 50 years old with persistent medial knee pain. Previous diagnosis had showed the presence of medial osteoarthritis. More recent radiographs had showed marked medial joint narrowing. The femur and tibia were about at 180°. It was decided to correct by about 5°.

The patient was given a spinal anaesthetic and positioned on her left side with a lateral aspect of her right leg facing up. A tourniquet was applied to the leg which was draped. Using the fibular head and patella as landmarks, an anterior to posterior incision was made about 1" below the joint line. A number 16 needle was then placed in the joint line to serve as a further landmark. Great care was taken to avoid the posterior aspect of the fibular head and all tissue and muscle was resected from the wedged site. A tape measure was used to mark the wedged site.

Most of the fibular head was removed, a procedure necessary to avoid the fibula holding the wedge site open. The wedge was cut free-hand using a jigsaw-type blade. The cut was carried out medially until the blade contacted the cortex. It is desirable not to cut all the way across the tibia. The bone was tidied using standard surgical instruments and the fit of the bone was checked by applying valgus stress to the leg. The leg was elevated at the foot so that gravity applied the valgus stress to the bone.

A stepped staple was hammered in to hold the wedge closed. A second staple with no step was also applied slightly posterior of the first. The wound was cleaned and the incision closed. A dressing was applied to the incision site.

In a conventional procedure a web roll would be applied as an underlay for a synthetic cast. With the leg still elevated for valgus stress, two rolls of 5 inch synthetic casting material would be applied to form a short leg cast with 20° of flexion. In these circumstances, the knee would be kept in the cast for four to six weeks. The cast could be changed if it becomes too loose but the knee would be immobilized.

According to the present invention, a brace would have been fitted to the patient prior to the operation. In those circumstances, subsequent to the application of the dressing, the brace would be refitted to the patient and adjusted by the surgeon using the procedure described above, that is screws 54 and 62 would be loosened and tightened as appropriate until the surgeon's satisfaction to achieve bracing of the knee without immobilizing of the knee. Adjustment of the brace can be carried out with extreme ease at any time, at the surgeon's discretion.

Figure 12:
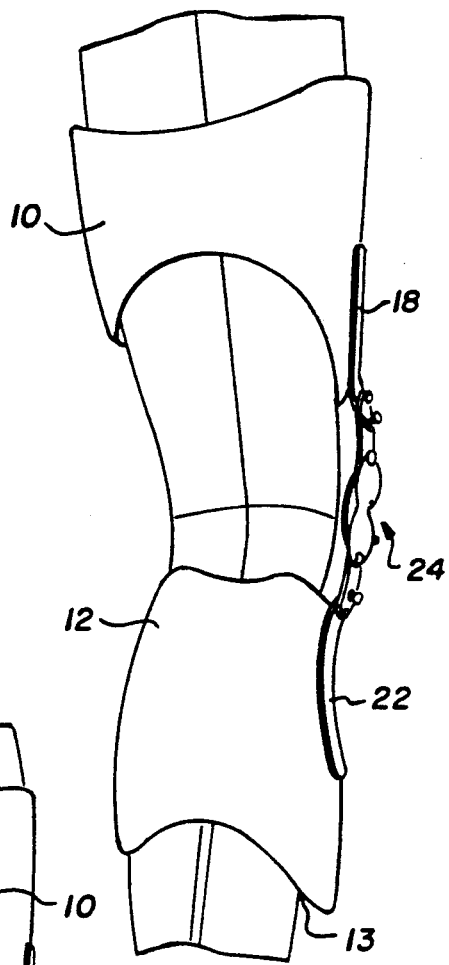
Figure 13:
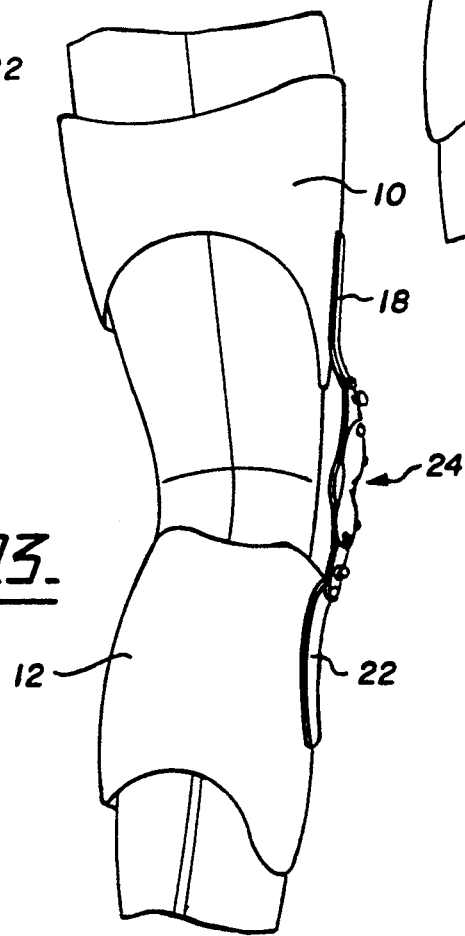

FIGS. 11 to 13 illustrate the various steps in the method according to the present invention. The brace generally illustrated in these drawings is the brace of FIG. 2 and 3.

FIG. 11 shows the leg prior to the operation. The brace is fitted accurately. In particular it will be noted that cuffs 10 and 12 fit the thigh and calf of the patient respectfully. Screws 54 and 62 are adjusted to ensure that that position is properly established.

FIGS. 12 and 13 show the leg after high tibial osteotomy. In FIG. 12 the brace is adjusted as in FIG. 11. That is the brace is as fitted to the leg prior to the osteotomy. Because of the wedge removed, cuff 12 no longer fits properly. Note in particular the gap 13. As a result the brace is adjusted, as described above, so that the cuff 12 and the cuff 10 both fit properly and the gap 13 is eliminated. This arrangement is shown in FIG. 13.

The embodiment of FIGS. 2 and 3 is generally illustrated in FIGS. 11 to 13 but precisely the same considerations apply in all other embodiments of the invention.

Using the present invention, the knee is not immobilized as it would be with a cast. The knee can move while fully supported. However, the knee is also securely braced. The degree of movement of the knee can be controlled in a manner known with braces of the sort illustrated in the drawings.

Adjustment of the relative inclination of the cuffs to the pivot can easily be carried out.

I claim:

1. In an orthopaedic brace comprising:
    a pair of arms to be secured to a wearer's body, a pivotable joint between said arms to allow pivoting of the knee while supporting the knee, the improvement comprising:
    joint means in the brace for allowing controlled medial and lateral inclination of each arm relative to the pivotable joint.

2. A brace as claimed in claim 1 in which there is a joint means in each arm, formed adjacent the pivotable joint of the brace.

3. A brace as claimed in claim 2 in which each arm is formed in at least two parts, a first part and a second part:
    a tab on the first part; and
    an opening in the second part to receive the tab;
    means to secure the first and second parts together and to lock them in a predetermined position; and
    means to move the first and second parts relative to each other to set the predetermined position.

4. A brace as claimed in claim 3 having a threaded opening in the tab;
    a screw to extend through the threaded opening to abut said second part of the arm;
    whereby turning of the screw to move it into the threaded opening acts to separate said tab and said second part of the arm.

5. A brace as claimed in claim 3 in which the means to secure the parts and to lock the parts in a predetermined position comprises a clear opening adjacent the opening in said second part and a threaded opening in said first part, tightening of the screw into the threaded opening acting to lock the first and second parts of the arm together.

6. A brace as claimed in claim 1 in which the joint means to allow controlled inclination of each arm relative to the pivotable joint comprises a hinge formed in the pivotable joint.

7. A brace as claimed in claim 6 in which the pivotable joint is formed in a first and a second part, the hinge being formed in two parts, one part attached to the first part of the pivotable joint and a second part attached to the second part of the pivotable joint:

at least one of said parts of the hinge being internally threaded;

a threaded hinge pin extending through the first and second parts, slackening and tightening of the pin in the threaded part allowing setting and locking to control the inclination of each arm relative to the pivotable joint.

8. A brace as claimed in claim 7 in which the first and second parts of the hinge abut each other at internal surfaces;

mutually engagable serrations at the internal faces to assist locking at a predetermined position.

9. A brace as claimed in claim 2 in which the joint means in each arm is a hinge.

10. A brace as claimed in claim 9 in which each arm is formed in at least two parts, a first part and a second part;

each hinge being formed in two parts with a first part of the hinge attached to the first part of each arm and a second part of each hinge attached to a second part of each arm;

means to secure the first and second parts together and to lock them in a predetermined position.

11. A brace as claimed in claim 10 in which the means to secure the first and second parts together comprises at least one of said hinge parts being threaded;

a threaded hinge pin extending through the first and second parts of the hinge whereby slackening and tightening of the pin in the threaded part of the hinge allows setting and locking of the first and second parts of each arm relative to each other to set the predetermined position.

12. A brace as claimed in claim 10 in which the first and second parts of each hinge abut each other at internal faces;

mutually engagable serrations at the internal faces to assist locking at the predetermined position.

13. A brace as claimed in claim 10 in which the means to secure the first and second parts of each arm together and to lock them in a predetermined position comprises a tab on the first part extending over the second part;

means to secure the first and second parts together and to lock them in a predetermined position; and means to move the first and second parts relative to each other to set the predetermined position.

14. A brace as claimed in claim 13 in which there is a threaded opening in the tab;

a screw to extend through the threaded opening to abut said second part of the arm;

whereby turning of the screw to move it into the threaded opening acts to separate said tab and said second part of the arm.

15. A brace as claimed in claim 13 in which the means to secure the parts and to lock the part in a predetermined position comprises a clear opening in said second part and a threaded opening in said first part, tightening of the screw into the threaded opening acting to lock the first and second parts of the arm together.

16. A method of bracing a knee of a patient following high tibial osteotomy comprising:

locating a brace about the knee, said brace having a pair of arms to contact the leg of the patient and a pivotable joint between said arms to allow pivoting of the knee while supporting the knee, a joint in the brace to allow controlled medial and lateral inclination of each arm relative to a pivotable joint; and adjusting the inclination to provide the required bracing at the required inclination.

17. A method as claimed in claim 16 including locking the inclination once the desired adjustment has been achieved.

* * * * *

REEXAMINATION CERTIFICATE (3290th)

United States Patent [19]

Taylor

[11] B1 5,302,169
[45] Certificate Issued Aug. 5, 1997

[54] POST OPERATIVE KNEE BRACE

[75] Inventor: Dean A. Taylor, Vancouver, Canada

[73] Assignee: Generation II Orthotics Inc., Richmond, Canada

Reexamination Request:
No. 90/004,258, May 30, 1996

Reexamination Certificate for:
Patent No.: 5,302,169
Issued: Apr. 12, 1994
Appl. No.: 1,204
Filed: Jan. 4, 1993

[51] Int. Cl.$^6$ .................................................. A61F 5/00
[52] U.S. Cl. .................................................. 602/16; 602/26
[58] Field of Search .................................................. 602/5, 16, 23, 602/26, 62; 128/882, 898; 623/27, 39

[56] References Cited

U.S. PATENT DOCUMENTS

| | | | |
|---|---|---|---|
| 1,336,695 | 4/1920 | Gromes | 602/16 |
| 1,381,290 | 6/1921 | Diadul. | |
| 1,418,283 | 6/1922 | Cameron | 602/16 |
| 1,885,448 | 11/1932 | Jones | 602/16 |
| 4,632,098 | 12/1986 | Grundei. | |
| 4,821,707 | 4/1989 | Audette. | |
| 4,881,532 | 11/1989 | Borig. | |
| 5,002,045 | 3/1991 | Spademan. | |
| 5,056,509 | 10/1991 | Swearington. | |
| 5,086,760 | 2/1992 | Neumann. | |
| 5,107,824 | 4/1992 | Rogers et al. | 602/16 |
| 5,302,169 | 4/1994 | Taylor. | |

FOREIGN PATENT DOCUMENTS

| | | |
|---|---|---|
| 357243 | 8/1922 | European Pat. Off.. |
| 2 239 382 | 8/1972 | European Pat. Off.. |
| 0 301 817 | 7/1988 | European Pat. Off.. |
| 2163352 | 2/1986 | United Kingdom. |
| WO94/15555 | 7/1994 | WIPO. |

*Primary Examiner*—Linda C. M. Dvorak

[57] ABSTRACT

An orthopaedic brace having a pair of arms to be secured to wearer's body. There is a pivotable joint between the arms to allow pivoting of the knee while supporting the knee. According to the invention there is a joint in the brace to allow controlled inclination of each arm relative to the pivotable joint. A method of bracing a knee following high tibial osteotomy is also disclosed. According to the method aspect the brace as described above is located about the knee and the arms are adjusted to allow controlled inclination of each arm relative to the pivotable joint to provide the required bracing of the required inclination.

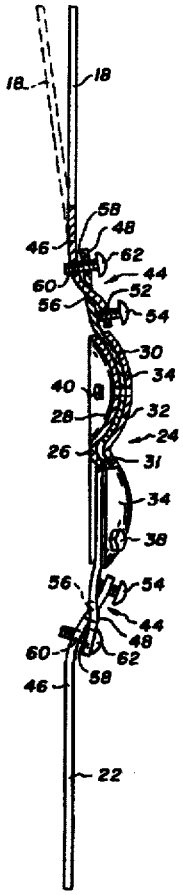

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 16 and 17 is confirmed.

Claim 1 is determined to be patentable as amended.

Claims 2–15, dependent on an amended claim, are determined to be patentable.

New claims 18–21 are added and determined to be patentable.

1. In an orthopaedic knee brace comprising:
    a pair of *substantially rigid* arms to be secured to a wearer's body, a pivotal joint between said *rigid* arms to allow pivoting of the knee while supporting the knee, the improvement comprising:
    joint means in the brace to allow controlled medial and lateral inclination of each *rigid* arm relative to the pivotal joint.

*18. The knee brace of claim 1 wherein the rigid arms extend substantially linearly from the pivotal joint toward the wearer's body.*

*19. The knee brace of claim 1 wherein the rigid arms are sized and configured to extend from the pivotal joint to locations directly above and below the wearer's knee to provide support to the knee against lateral loads applied to the knee.*

*20. An orthopaedic knee brace able to support the knee, the brace comprising:*

*first and second support members to be attached to a wearer's leg immediately above and below the wearer's knee;*

*a substantially rigid arm attached to each support member to extend from the respective support member towards the knee when the brace is worn;*

*a pivotable joint between the rigid arms for allowing pivoting of the knee; and*

*adjustable joint means located between the rigid arms for allowing controlled medial and lateral inclination of each rigid arm relative to the pivotable joint.*

*21. An orthopaedic knee brace for laterally supporting the knee, the brace comprising:*

*a pivotable joint for allowing pivoting of the knee;*

*first and second substantially rigid arms attached to the pivotable joint, each support member extending substantially linearly from the pivotable joint to a location directly above and below the wearer's knee when the brace is worn to laterally support the knee; and*

*an adjustable joint coupled to each rigid arm for allowing controlled medial and lateral inclination of each rigid arm relative to the pivotable joint.*

\* \* \* \* \*